United States Patent
Lemkin (10) Patent No.: US 10,976,293 B2
(45) Date of Patent: Apr. 13, 2021

(54) AGRICULTURAL PROCESSING SYSTEM AND METHOD

(71) Applicant: Mark Alan Lemkin, Berkeley, CA (US)

(72) Inventor: Mark Alan Lemkin, Berkeley, CA (US)

(*) Notice: Subject to any disclaimer, the term of this patent is extended or adjusted under 35 U.S.C. 154(b) by 312 days.

(21) Appl. No.: 15/766,810

(22) PCT Filed: Dec. 30, 2017

(86) PCT No.: PCT/US2017/069152
§ 371 (c)(1),
(2) Date: Apr. 7, 2018

(87) PCT Pub. No.: WO2019/133014
PCT Pub. Date: Jul. 4, 2019

(65) Prior Publication Data
US 2019/0204283 A1    Jul. 4, 2019

(51) Int. Cl.
*G01N 33/00* (2006.01)
*B01L 7/00* (2006.01)
(Continued)

(52) U.S. Cl.
CPC ............ *G01N 33/0098* (2013.01); *B01L 7/00* (2013.01); *G01N 1/44* (2013.01); *G01N 7/16* (2013.01); *G01N 11/02* (2013.01); *G01N 33/004* (2013.01); *B01L 2200/146* (2013.01); *B01L 2200/147* (2013.01); *B01L 2300/041* (2013.01);
(Continued)

(58) Field of Classification Search
CPC ...... A01H 6/28; G01N 33/0098; C07C 51/38; C07C 67/32; C07C 45/48
See application file for complete search history.

(56) References Cited

U.S. PATENT DOCUMENTS 5,571,401 A    12/1996 Lewis et al.
5,698,089 A    12/1997 Lewis et al.
(Continued)

FOREIGN PATENT DOCUMENTS

WO    WO 2017/040836    3/2017

OTHER PUBLICATIONS

Zulkeflee, Zufarzaana, and Antoni Sánchez. "Solid-state fermentation of soybean residues for bioflocculant production in a pilot-scale bioreactor system." Water science and technology 70.6 (2014): 1032-1039. (Year: 2014).*

(Continued)

*Primary Examiner* — Robert J Eom (57) ABSTRACT

A method and device for processing an agricultural product is provided. The device includes a chamber having an opening, and a heater operative to heat the contents of the chamber. A sensor having an output is coupled to the chamber, the sensor output being processed to provide information about at least one of: a state of decarboxylation, or a quantity of a material in the contents of the chamber. The method includes loading a quantity of the agricultural product in a chamber having an port and applying an elevated temperature to the chamber to increase a rate of decarboxylation. A property of a gas is measured at the port the measurement being processed to determine one of either: a state of decarboxylation, or a quantity of material in the sample.

23 Claims, 9 Drawing Sheets

(51) Int. Cl.
  *G01N 1/44* (2006.01)
  *G01N 11/02* (2006.01)
  *G01N 7/16* (2006.01)

(52) U.S. Cl.
  CPC . *B01L 2300/049* (2013.01); *B01L 2300/0627* (2013.01); *B01L 2300/1805* (2013.01)

(56) References Cited

U.S. PATENT DOCUMENTS

| | | |
|---|---|---|
| 5,788,833 A | 8/1998 | Lewis et al. |
| 5,891,398 A | 4/1999 | Lewis et al. |
| 5,911,872 A | 6/1999 | Lewis et al. |
| 5,951,846 A | 9/1999 | Lewis et al. |
| 5,959,191 A | 9/1999 | Lewis et al. |
| 6,010,616 A | 1/2000 | Lewis et al. |
| 6,013,229 A | 1/2000 | Lewis et al. |
| 6,093,308 A | 7/2000 | Lewis et al. |
| 6,170,318 B1 | 1/2001 | Lewis |
| 6,290,911 B1 | 9/2001 | Lewis et al. |
| 6,350,369 B1 | 2/2002 | Lewis et al. |
| 6,387,329 B1 | 5/2002 | Lewis et al. |
| 6,455,319 B1 | 9/2002 | Lewis et al. |
| 6,571,603 B1 | 6/2003 | Doleman et al. |
| 6,610,367 B2 | 8/2003 | Lewis et al. |
| 6,631,333 B1 | 10/2003 | Lewis et al. |
| 6,759,010 B2 | 7/2004 | Lewis et al. |
| 6,773,926 B1 | 8/2004 | Freund et al. |
| 6,962,675 B2 | 11/2005 | Lewis et al. |
| 7,122,152 B2 | 10/2006 | Lewis et al. |
| 7,144,553 B2 | 12/2006 | Lewis et al. |
| 7,156,985 B1 * | 1/2007 | Frisch .............. C02F 3/006 210/150 |
| 7,189,353 B2 | 3/2007 | Lewis et al. |
| 7,175,885 B2 | 12/2007 | Lewis et al. |
| 7,359,802 B1 | 4/2008 | Lewis et al. |
| 7,595,023 B2 | 9/2009 | Lewis et al. |
| 7,955,561 B2 | 6/2011 | Lewis et al. |
| 7,966,132 B2 | 6/2011 | Lewis et al. |
| 8,394,330 B1 | 3/2013 | Lewis et al. |
| 9,291,552 B2 | 3/2016 | Cowger et al. |
| 2005/0153436 A1 * | 7/2005 | Vilendrer ............... C12M 41/46 435/289.1 |
| 2016/0340629 A1 | 11/2016 | Winnicki et al. |

OTHER PUBLICATIONS

De Backer, Benjamin, et al. "Innovative development and validation of an HPLC/DAD method for the qualitative and quantitative determination of major cannabinoids in cannabis plant material." Journal of Chromatography B 877.32 (2009): 4115-4124. (Year: 2009).*
Waters 2996 PDA Detector Operator's Guide, Waters, Revision C, https://www.waters.com/webassets/cms/support/docs/71500023202rc.pdf.*
Agilent 1100 Series Thermostatted Column Compartment Reference Manual, Agilent Technologies, Edition Jul. 2002, https://www.aimanalytical.com/Manuals/1100ThermColumn.pdf.*
Agilent 1100 Series Standard, Micro and Preparative Autosamplers Reference Manual, Agilent Technologies, Edition Aug. 2001, https://www.meadowshplc.com/sites/default/files/products/attachments/1100_reference_manual.pdf.*
Agilent 1200 Series Quaternary Pump User Manual, Agilent Technologies, Edition Nov. 2008, https://www.agilent.com/cs/library/usermanuals/public/G1311-90011_QuatPump_ebook.pdf.*
Agilent 1100 Micro Vacuum Degasser Reference Manual, Agilent Technologies, Edition Jun. 2000, https://www.aimanalytical.com/Manuals/1100%20Micro%20degas.pdf.*

* cited by examiner

AGRICULTURAL PROCESSING SYSTEM AND METHOD

TECHNICAL FIELD

This disclosure generally relates to processing of agricultural products, and more particularly to the decarboxylation or the assaying of agricultural products containing a cannabinoid.

DESCRIPTION OF RELATED ART

There are many different types of cannabinoid acids naturally occurring in agricultural products such as *Cannabis sativa*, certain types of *Echinacea, Acmella oleracea, Helichrysum umbraculigerum*, and *Radula marginata*. Naturally-produced cannabinoid acids include CBDA (Cannabidiolic Acid), CBGA (Cannabigerolic Acid), CBCA (cannabichromenic acid), and THCA (Tetrahydrocannabinolic acid), among others. The amounts of these acid forms of cannabinoids vary from plant to plant due to growing conditions, genetics, harvest timing, and harvest techniques. Many cannabinoids derive increased therapeutic benefits by decarboxylation of the acid form, thereby converting the cannabinoid to a neutral form, which is active in the body. Because the amount of cannabinoids in a sample can vary substantially, knowing the concentration of cannabinoid or cannabinoid acids is important to ensure proper dose control.

Measurement of neutral-cannabinoid or cannabinoid-acid concentration is conventionally determined using laboratory techniques such as high-performance liquid chromatography (HPLC); gas chromatography (GC); or diffuse reflectance near infrared (DRNIR) spectroscopy. However, these measurement techniques are generally performed on a raw sample, generally are performed using only a very small sample size, and are quite expensive. Knowing the quantity of a cannabinoid acid in a raw sample is somewhat useful in that it indicates the maximum potential neutral cannabinoids that one could theoretically attain under perfect decarboxylation conditions; however, the actual amount of neutral cannabinoids after processing, (e.g. cooking, vaporizing, converting to a tincture, smoking) is unknown without further measurements. For many applications the neutral form of the cannabinoid is the desired active compound and therefore knowledge of the content of the original acid cannabinoids is of limited use. Sampling of cannabinoid profiles generally uses a very small quantity, on the order of a gram. As the cannabinoid content of a single plant (e.g. *Cannabis sativa, Cannabis sativa forma indica*) may vary dramatically over the location on the plant (e.g. shaded portions of the plant may generate lower concentration of cannabinoids—variations of 20% are not uncommon) such a small sample size provides only limited information as to the overall cannabis content. Furthermore the samples after processing for HPLC are generally unsuitable for consumption as the preparation includes mixing the sample with a solvent and are therefore wasted. Presently available techniques are expensive at least in part because these techniques require trained laboratory personnel and expensive lab equipment and reagents.

SUMMARY

Decarboxylation is a process in which a chemical change occurs to an acid-form of a molecule to convert it to a neutral form of the molecule. Application of an elevated temperature can accelerate the decarboxylation process. When a cannabinoid acid is to be converted to a neutral form, complete conversion is desired as the cost of the starting plant material can be quite considerable.

For example, if a quantity of cannabis having 10 grams of CBDA is to be converted to CBD and only half of the CBDA completes decarboxylation, then half of the material is wasted, as it remains in a non-bioavailable form. On the other hand, application of excess heat is undesirable as the neutral forms of cannabinoids can start to degrade with further heating.

In accordance with an embodiment described herein, a system for processing an agricultural product comprises a chamber having an opening, a heater operative to heat the contents of the chamber, and a sensor having an output, with the sensor coupled to the chamber. The sensor output is processed to provide information about at least one of: a state of decarboxylation, or a quantity of a material in the contents of the chamber.

In some embodiments the information includes information about the quantity of an acid-cannabinoid or a neutral-cannabinoid in the chamber.

The agricultural product may include: *Acmella oleracea, Cannabis sativa, Cannabis sativa forma indica, Echinacea, Helichrysum umbraculigerum,* or *Radula marginata*.

In some embodiments the sensor output is responsive to carbon dioxide concentration, chamber pressure, a flow rate, or a temperature. The sensor may include a pressure sensor, a bubbler, an orifice, a carbon-dioxide sensor, or an infra-red flow sensor.

In some embodiments the system further includes a valve.

The system may include a lid with a seal, with a pressure sensor coupled to the interior of the chamber via a port.

In some embodiments the system further includes a fan and a second opening. The fan induces a flow from the second opening, past a heater, over the agricultural contents and out the first opening. The sensor may detect carbon dioxide concentration at the first opening. A second sensor responsive to carbon dioxide, located proximate the second opening, may also be included.

The chamber walls may be insulated or comprise a vacuum flask; the chamber may have a thermally conductive lid.

In some embodiments a temperature sensor is coupled to the chamber. A processor is coupled to the temperature sensor, and the sensor having an output coupled to the chamber is a pressure sensor. The processor controls the chamber temperature to vary between at least two temperatures while monitoring the pressure. The processor processes these data to detect a property of at least two different cannabinoids in the chamber.

In accordance with an embodiment described herein, a method for processing an agricultural product comprises loading a quantity of the agricultural product in a chamber having an port; applying an elevated temperature to the chamber to increase a rate of decarboxylation; measuring a property of a gas at the port; and, processing the measurement to determine one of either: a state of decarboxylation, or a quantity of material in the sample.

An additional step of sealing a lid may be included, after the step of loading a quantity of the agricultural product. The lid remains sealed until the temperature returns to ambient conditions. In this embodiment, the step of measuring a property of the gas at the port is a pressure measurement.

An additional step of sealing a lid may be included, after the step of loading a quantity of the agricultural product. The lid remains sealed until the temperature returns to ambient conditions. In this embodiment, the step of measuring a property of the gas at the port is a mass-flow rate from the chamber to the ambient through a port.

In some embodiments the lid isn't sealed, and the step of applying an elevated temperature to the chamber comprises forcing air from an input port past a heating element into the chamber.

In some embodiments the step of measuring a property of the gas at the port comprises measuring carbon dioxide concentration. In some embodiments an additional measurement of carbon dioxide concentration at the input port is used.

In accordance with an embodiment described herein, a system for processing an agricultural product comprises a chamber having an opening. A heater, operative to heat the contents of the chamber, is coupled to the chamber. A first sensor having an output is coupled to the chamber, as is a temperature sensor having an output. A processor having first- and second-inputs and an output is coupled to the first-sensor output and the temperature-sensor having an output. The processor output is coupled to one of either a valve, or the heater operative to heat the contents of the chamber. The first sensor output may be responsive to at least one item selected from group consisting of: carbon dioxide concentration, chamber pressure, a flow rate, and a temperature.

BRIEF DESCRIPTION OF DRAWINGS

The figures listed below illustrate exemplary embodiments, and are not intended to cover all possible embodiments, including embodiments with additional or fewer components, steps, or connections. The embodiments, techniques, components, connections, and other teachings described in the figures are exemplary and were chosen to provide a clear explanation without unnecessary obfuscation.

DETAILED DESCRIPTION

Plant material loaded into a decarboxylation chamber, or simply a chamber, is hereby termed a charge, or a charge of material. The amount of time required for complete decarboxylation of the charge depends on at least the temperature. Excessive heat applied to the charge causes degradation of cannabinoids into other compounds different than the desired active compound, as well as excess loss of terpines. Material having differing density can have different thermal time constants in the chamber as well; therefore, it is difficult to determine when decarboxylation is complete by just monitoring and/or controlling the temperature of a decarboxylation chamber.

In some embodiments a vacuum flask, or Dewar flask, similar in construction to a vacuum-insulated food jar conventionally used for keeping packed lunches warm, is used as a decarboxylation chamber. In various embodiments the chamber comprises metal, glass, coated glass or metal, or glass having at least one mirror-like surface. Unlike a chamber insulated with foam, fiberglass, or other material, a vacuum flask includes at least a partial vacuum between an inner chamber wall and an outer wall, thereby removing thermal conduction (in accordance with the quality of the vacuum) as a potential thermal-loss mechanism. Since thermal radiation is quite low at normal decarboxylation temperatures the heat loss from the chamber becomes quite small allowing for a fast thermal time constant and a more uniform chamber temperature. Providing heat from the internal portion of the vacuum flask, as opposed to between the inner chamber and outer wall, improves manufacturability and thermal performance as the heating element doesn't have to include any portion in the vacuum space between the inner-chamber wall and the outer-chamber wall; including components in this region can result in outgassing, thereby reducing vacuum, as well as provide additional thermal conduction paths. In some embodiments the chamber includes a top comprising a heater, and a seal between the top and the chamber wherein, after the charge is loaded into the chamber, the top is affixed to the chamber (e.g. by screw, clamp, etc.) thereby providing an airtight seal, allowing carbon dioxide, water vapor, or other gasses to be quantified as they leave a port as described later. In various embodiments the seal comprises neoprene, EPDM, silicone, an elastomer, a plastic, rubber, a gasket, a metal gasket, a crush gasket, or any other suitable material. In various embodiments the lid comprises a thermally conductive material, for at least a portion of the lid, such as aluminum, copper, iron, or steel.

Figure 1:
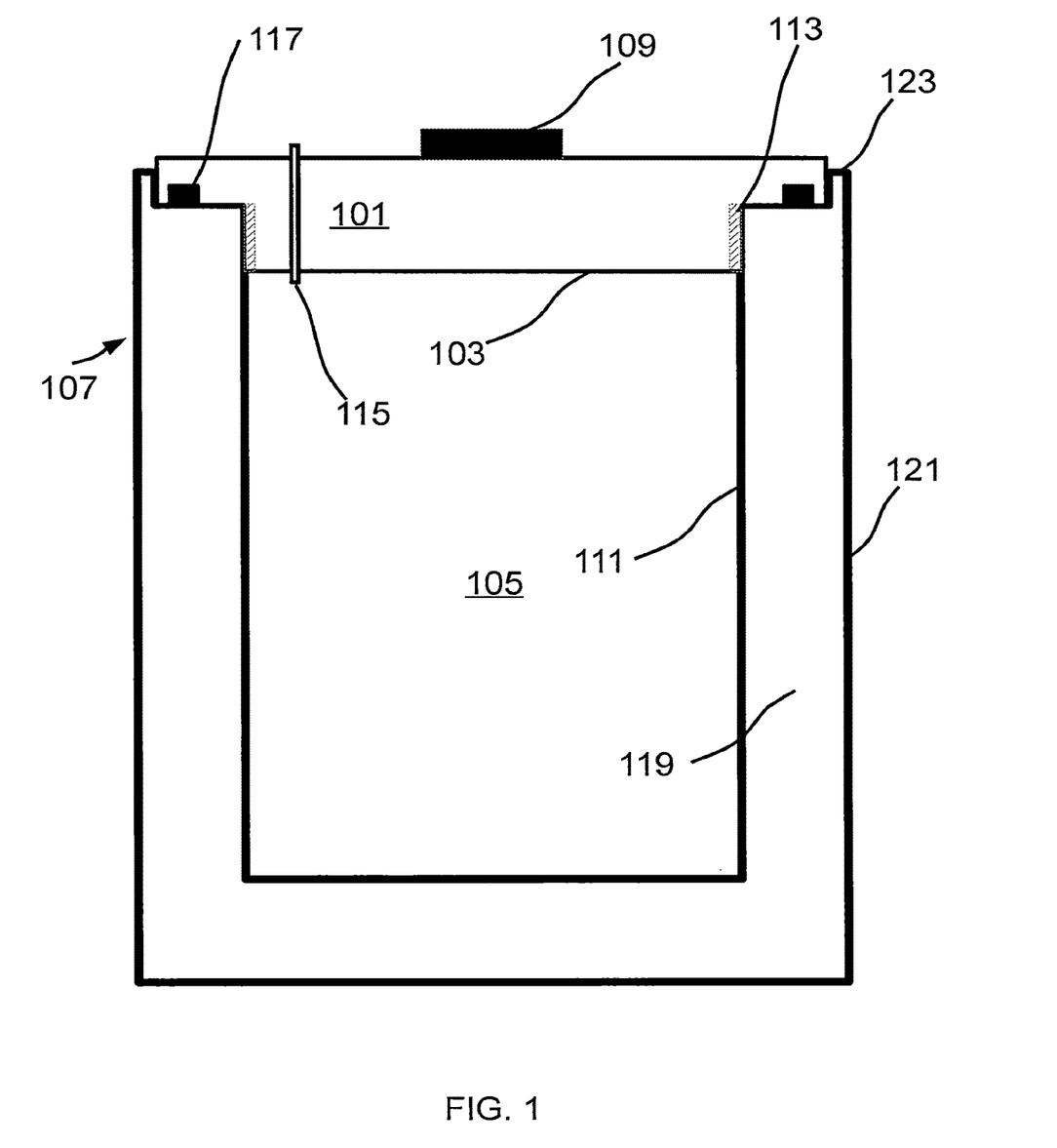
FIG. 1 illustrates a schematic diagram of a first embodiment of a decarboxylator.

FIG. 1 illustrates a first embodiment of a decarboxylator. Top 101 comprises a heating plate 103 that faces into the chamber 105 of vacuum flask 107. Vacuum flask 107 comprises an outer shell or wall 121, an inner wall 111, and an evacuated space 119; the outer and inner walls meet at lip 123. Heating plate 103 is made from a thermally conductive material, for example: copper, steel, or aluminum. Heater 109, comprising a resistive element or Peltier device, is located on the opposite side of the heating plate and is thermally coupled to the plate. In some embodiments thermal coupling includes thermal grease to improve heat transfer characteristics, a mechanical clamp that holds the resistor in contact with the heating-element plate, or a combination thereof. In some embodiments a thermal bridge between the top or heating plate and the inner chamber walls is formed when the top is affixed, thereby transferring heat from the heater to the inner wall 111 of the vacuum flask 107 with a low thermal resistance. In particular, a vacuum flask with an inner wall made of metal will conduct heat effectively from plate 103 through the inner wall 111, thereby completely surrounding the charge with an approximately equal temperature. For example, in some embodiments the plate extends to a screw 113 (e.g. threaded portion) that makes contact with the inner chamber wall 111 when the lid is closed; a thermal bridge may also be formed using a metal spring or brush affixed to the heating element plate that makes contact with the inner vacuum-flask wall upon closing. Top 101 also includes a port 115 coupled between chamber 105 and the atmosphere. The port, which may be a narrow metal tube, provides a path for gasses generated or expanded (e.g. by heating) inside chamber 105 to leave the chamber for mass detection, as described later. Seal 117 prevents gasses from leaving the chamber via a path other than the port.

Note that seal 117 doesn't prevent gasses, such as air, from leaving or entering the chamber, but rather seal 117 limits the path by which gasses enter or leave the chamber to port 115 so that they may be quantified, or that a positive- or a negative-pressure doesn't build up beyond a threshold in the chamber. In some embodiments, allowing gasses to freely exchange into and out of the chamber purges oxygen from the chamber due to thermal expansion, or due to displacement with generated carbon dioxide and steam vapor. For example, simply by heating air from a temperature of 25 C to 100 C will cause about 20% of the oxygen to leave the chamber through the port due to the expansion of the oxygen according to the ideal gas law. Furthermore, moisture in the charge, which may average about 5% to 10% by weight is converted to steam at approximately 100 C further displacing oxygen from the chamber. For example, given a charge mass of 25 grams that occupies a volume of 500 ml, a 5% moisture content would result in about 1.5 liters of water vapor (e.g. steam), which will purge the oxygen from the chamber as the water vapor leaves the port. Thus, allowing gases to escape through a port removes oxygen from the chamber to a level below the initial value at a point of sealing providing a lower oxygen content. On the other hand, the temperature will fluctuate during the decarboxylation process, which can cause positive or negative pressure to build up if gas exchange is prevented. Thus, in some embodiments air, or ambient gasses containing oxygen, enters the chamber via the port while the charge or chamber is at an elevated temperature, for example as the chamber temperature dips during a temperature cycle. However, oxygen that enters the chamber during the decarboxylation process via the port is quickly purged, as water vapor or the carbon dioxide generated from the decarboxylation process itself purges the oxygen from the chamber.

Figure 2A:
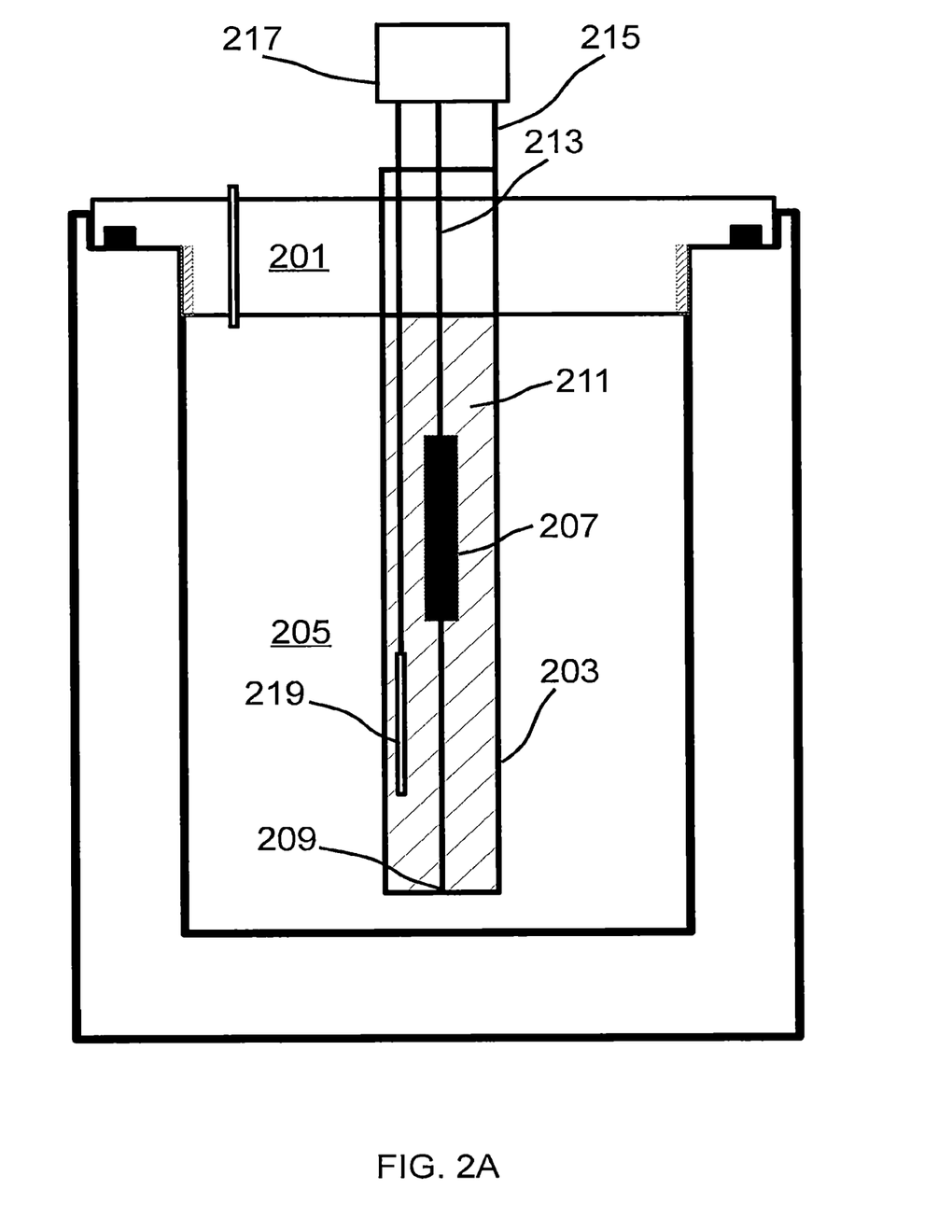
FIG. 2a illustrates a schematic diagram of a second embodiment of a decarboxylator with a heating tube.

In another embodiment, with reference to FIG. 2a, top 201 comprises a heating tube 203 that protrudes into the chamber 205; top 201 may be made of an insulating material such as plastic or a thermally-conductive material such as metal. Heating element tube 203 is made from a conductive material such as copper, steel, or aluminum. A heating element, 207, which may comprise e.g. a resistor, or a nonlinear resistor such as a tungsten filament, a Ni-Chrome wire, or a light bulb, is located internal to heating element tube 203 and is electrically connected to the tube at the end 209; in some embodiments the heating element is electrically connected to a first insulated wire (not shown) instead of the tube at the end. Thermal grease, 211, which in some embodiments includes a zinc oxide or aluminum oxide filler material, is placed in the space between the resistor and inner heating-element tube wall thereby providing a low thermal-resistance path to the tube wall. The other end of heating element 207 is connected to a second wire 213, which may include insulation to prevent incidental contact with the heating element tube wall. The wire, in conjunction with an additional electrical connection to the heating element tube 215 (or insulated wire when a connection to the tube end is not used), are the terminals for the heater and are controlled by a processor 217, which controls the heater via a relay, transistor, switch, GPIO, or any other suitable mechanism. Heating element tube 203 also includes inside one or more temperature measuring devices 219, such as a thermocouple or a thermistor, which may be used to control the temperature using a feedback loop by the processor. In some embodiments the feedback loop is an analog feedback loop not involving a processor (e.g. a feedback loop constructed using one or more opamps or comparators). In some embodiments the temperature-measuring device is located at a different location, internal to the decarboxylation chamber, than the heating element tube, such as protruding from the lid, or recessed into the lid. A thermal fuse or thermal switch may be included in series with the heating element to prevent a hazardous fault condition: if the temperature at the thermal fuse or thermal switch rises above the rated fuse temperature the flow of electricity through the heating element is stopped thereby preventing overheating of the charge or reducing a fire hazard.

Figure 2B:
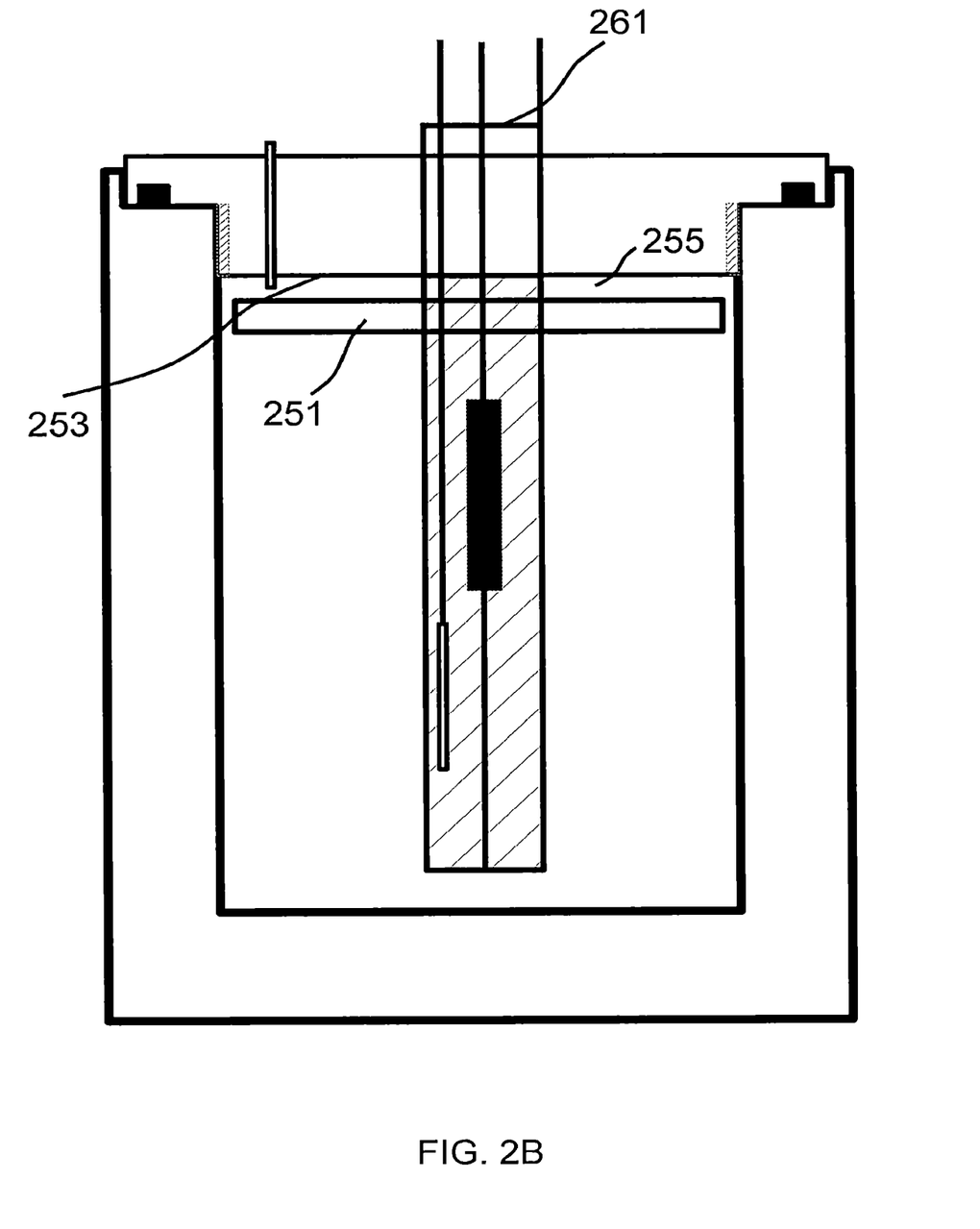
FIG. 2b illustrates a schematic diagram of a third embodiment of a decarboxylator with a thermally-conductive plate.

With reference to FIG. 2b, in some embodiments a thermally-conductive plate 251 (e.g. copper, aluminum, steel) is coupled to the heating tube below a bottom surface 253 of the top. Plate 251 provides a low-resistance thermal path in the radial direction of the chamber, thereby reducing thermal gradients caused by conduction through the bottom surface 253 of the top. An insulating layer 255 (such as an air gap, foam, or plastic) between plate 251 and surface 253 provides thermal insulation. While heat is lost though surface 253 at a rate substantially higher than through a vacuum, the thermal conductivity of e.g. copper is about 16,000 times higher than, e.g. air. Therefore, thermal gradients are minimized. In some embodiments a portion of the heating tube 261 is exposed to ambient conditions so as to provide a source of thermal loss for a class-A-style biasing scheme. Alternately, instead of directly exposing a portion of the heating tube to ambient, a class-A-style bias condition may be effected by choosing an insulation thickness to place on top of the portion of heating tube 261 that provides the desired heat loss characteristic.

Since a vacuum flask is an excellent insulator the chamber will remain at an elevated temperature for an extended period of time after the heater has been de-energized. In various embodiments a Peltier device coupled to the heating element tube or heating plate is used to cool the chamber after decarboxylation has completed; an alarm is sounded (i.e. a beep) to indicate the material should be removed; a vent is opened allowing circulation of room-temperature air through the chamber; or a fan is energized or remains energized upon completion. In some embodiments the heat input to the decarboxylation chamber is reduced in anticipation of complete decarboxylation as the decarboxylation nears completion so the chamber temperature is below a temperature threshold once decarboxylation has completed.

In some embodiments the lid or top comprises metal and includes a means of cooling to ambient conditions after heat ceases to be applied to the metal e.g. a radiator, a fan, an exposed, thermally-conductive surface (e.g. portion 261 of tube). By providing a way for the chamber to cool towards ambient temperature, the heat flow is effectively biased akin to a class-A amplifier in electronics: chamber temperature may be increased or decreased about the present temperature by controlling the amount of heat added to the lid in this embodiment. Cooling relative to the present temperature of the lid is accomplished not by actively removing heat from the lid but rather reducing the amount of heat added to the lid.

Figure 3:
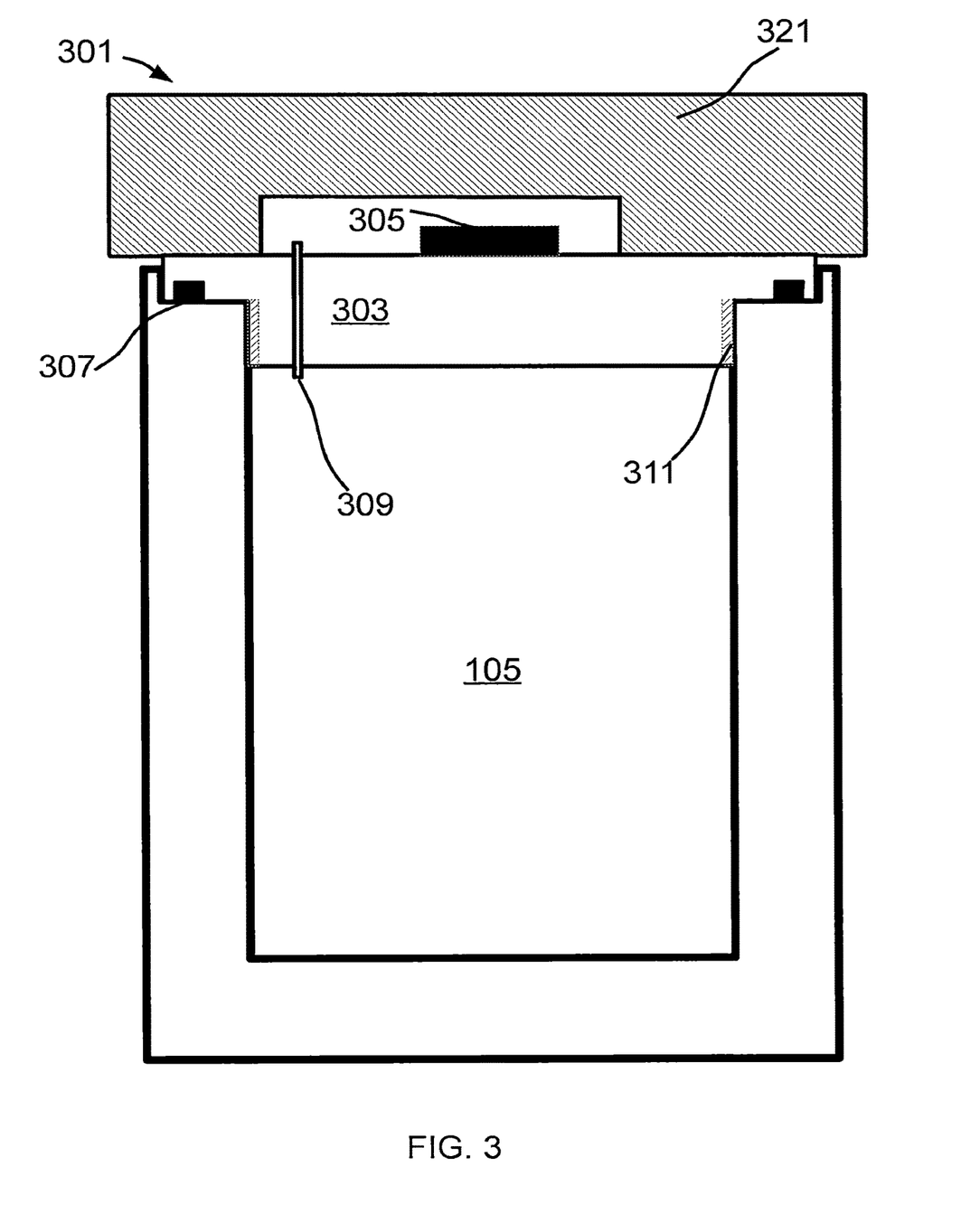
FIG. 3 illustrates a schematic diagram of a decarboxylator having a thermally isolated cover.

In some embodiments, as illustrated in FIG. 3, a lid 301 with a metal top 303 comprises a heater 305; and, a seal 307 makes contact with the chamber and prevents gasses from escaping at the interface thereby ensuring they leave through the port 309. Port 309 is connected to a flow measurement system outside of the chamber. Thermal bridge 311, in this case metal threads in the lid that interface with metal threads on the inner chamber wall, provides improved and more-even heating of the chamber walls and, thus, charge. In some embodiments a conductive tube as previously described or a passive tube made of metal without any heating elements is used to conduct heat towards the center of the chamber. Since the temperature of the lid can be in excess of 100 degrees C. a thermally isolated exterior cover 321 (e.g. made from plastic) is coupled to the lid thereby preventing direct contact of the physical lid by a user, improving safety, as well as reducing thermal loss from the top to ambient.

In some embodiments the quantity (e.g. mass) of gasses released during the decarboxylation process is determined and this quantity: is used to estimate the amount of cannabinoids in a sample; is used to determine a state of decarboxylation; or, is used for both purposes. As a single molecule of, e.g., CBDA is decarboxylated into CBD a single molecule of carbon dioxide ($CO_2$) gas is released in the process. Relating the amount of $CO_2$ released to the amount of neutral cannabinoids decarboxylated may be performed using stoichiometry; alternately, a functional relationship may be established between the acid form of the molecule, the neutral form of the molecule, and the amount of $CO_2$ released, for example by experimental measurements of released $CO_2$ from a plurality of reference plant materials decarboxylated in the chamber at an elevated temperature, and calibrated by pre- and post-decarboxylation HPLC test results in combination with a regression analysis.

As an example, using stoichiometry it may be found that CBDA has an approximate molar mass of 358 g/mol and the neutral form CBD has an approximate molar mass of 314 g/mol; the product of the reaction, $CO_2$, has a molar mass of 44 g/mol. Thus, if we determined that 1 gram of $CO_2$ was released during the decarboxylation process that would indicate that 7.1 grams of CBD were decarboxylated per the following relationship between $CO_2$ and CBD determined by stoichiometry:

$$\text{grams of neutral CBD} = (1 \text{ gram of } CO_2/(44 \text{ grams/mol of } CO_2))*(314 \text{ grams/mol of CBD})$$

Therefore, the amount of acid-cannabinoid decarboxylated to the neutral form may be determined by quantifying the mass of released gasses during decarboxylation and mathematically operating, or processing, this quantity. Alternately, or in addition, by monitoring the evolution of gasses when the charge is at a decarboxylation temperature, completion of the decarboxylation process may be determined, (e.g. by a determination that gas generation has dropped below a threshold, a rate of pressure increase in a closed chamber less than a threshold, or a gas flow rate below a threshold). Measurement of released gasses may be used to control the temperature over time in the decarboxylation chamber to ensure complete decarboxylation; quantifying the gasses released during this process allows a calculation of the total amount of acid-cannabinoids in the initial sample, or alternately the amount of neutral cannabinoids in the decarboxylated sample formed during the decarboxylation process. When combined with the mass or volume of the charge (e.g. measured by a scale or a known volume, such as a cup-measure used for cooking) a percentage by weight or volume may be determined, thereby allowing more accurate dosage to be determined. In general while the preponderance of cannabinoids found in raw plant matter are of the acid form, there may exist small quantities of neutral forms of these cannabinoids. Generally these quantities are small, often less than 1% of the total mass of flowers versus up to greater than 30% for the acid form of cannabinoid.

In some embodiments a mass-measuring sensor such as a load cell is coupled between a base and the outside of the decarboxylation chamber. The weight of the decarboxylation chamber is borne by the load cell. The load cell is tared or zeroed before the charge is loaded and measured again after the charge has been loaded allowing calculation of the mass of the charge.

Quantification of mass of gasses released may use any suitable method including mass inference using at least one of: chamber pressure, carbon-dioxide concentration, chamber temperature, atmospheric pressure, differential pressure, differential pressure across an orifice, gauge pressure, absolute pressure, temperature, a thermal mass-flow meter, volume-flow rate, or mass flow.

By monitoring the evolution of gasses from a decarboxylation chamber the present state of the decarboxylation process may be determined, as gas generation rate is directly dependent on the rate of decarboxylation of the acid compound. For example, upon reaching a decarboxylation temperature, which may or may not be precisely controlled, the rate of gas generation from the chamber is monitored. In some embodiments, the temperature is not directly regulated: the rate of heat addition into the decarboxylation chamber is instead controlled by the rate of gas generation in the chamber, or the rate of change of the rate of gas generation in the chamber, to maintain a target gas generation rate which changes over time as the charge becomes fully decarboxylated. The addition of heat to the chamber is constrained so the chamber operates within an operating temperature region to prevent the chamber temperature from reaching an undesirable temperature (for example, heat may be added to the chamber as needed to maintain a certain $CO_2$ flow rate as long as the chamber temperature doesn't rise above 130 degrees C.).

Over time there will be less cannabinoid acid to decarboxylate, as it has already been converted to neutral form; therefore, the rate of gas generation will decrease. When the decarboxylation is sufficiently complete the rate of gas generation will drop below a threshold indicating completion of the process.

In some embodiments the rate of gas generation for an initial quantity of a first cannabinoid acid at a constant temperature follows a first functional relationship (e.g. exponential, quadratic, cubic, linear) between time and gas generation rate; this first functional relationship also being dependent on temperature. Such a functional relationship may be determined by regression analysis of calibrated plant material (e.g. via HPLC) using a design-of-experiments process including time and temperature as variables.

In some embodiments the rate of gas generation for an initial quantity of a second cannabinoid acid at a constant temperature follows a second functional relationship (e.g. exponential, quadratic, cubic, linear) between time and gas generation rate; this second functional relationship also being dependent on temperature and also being a different functional relationship than the first functional relationship.

In some embodiments the charge includes at least two distinct cannabinoid acid forms (e.g. CBDA, THCA) each having a different functional relationship. By measuring the gas generation rate at a first known temperature (e.g. using a thermocouple) and the gas generation rate at a second known temperature the relative composition (e.g. percent concentration, apportionment of mass) of the cannabinoid acids in the sample may be inferred using the known first and second temperatures, the known first- and second gas-generation rate functional relationships, the measured gas generation characteristics, and the time history of these variables (e.g. time and temperature), for example by solving a system of equations expressing these relationships and quantities.

In some embodiments mass flow is inferred using a differential pressure measurement across an orifice, or a Venturi tube. In some embodiments mass flow is inferred by counting bubbles generated in a bubbler such as commonly used as an airlock to prevent microbial contamination when home-brewing beer; counting may use optical detection of movement (e.g. camera or breaking a light beam between a light source and a light detector), a magnet with a switch or sensor, an acoustic sensor, an accelerometer or any other appropriate sensor.

In some embodiments, mass is determined using a pressure sensor and valve where the valve is closed and the pressure is sampled with the valve in the closed position. Next, after the pressure reaches a threshold the valve is opened releasing the pressure. Because the volume and pressure before the valve is opened and after the valve is closed are both known, the mass lost through the valve when opened may be estimated using, for example, the ideal gas law. In some embodiments the rate of pressure rise between valve events (e.g. an open, a close) is used in conjunction with the ideal gas law, and a known chamber temperature to determine the mass generation rate of the gasses (e.g. using a direct pressure-rate calculation given two times and pressure values; using a measurement of the time between valve opening events given a pressure threshold at which point the valve is opened; using a count of the number of valve opening events, etc.). In some embodiments the valve is normally open and periodically closed for a time-period during which the pressure is monitored. After a time-period has elapsed the pressure is sampled and the valve opened; given the initial and final pressures and temperature over this sampling time the gas-generation rate may be determined using e.g. the ideal gas law. In some embodiments a calibration step is performed to improve accuracy of a mass measurement device by starting the empty decarboxylation chamber at a first known temperature, heating the chamber to a second known temperature, monitoring the mass flow rate through a port, and totalizing the mass flow; the ideal gas law provides the relationship of the initial air mass lost given the initial and final temperature and the chamber volume; this quantity is used to calibrate the mass flow sensor output.

As the chamber cools a negative pressure may form, meaning the chamber pressure may be lower than atmospheric pressure; this can make opening the chamber difficult, or damage a pressure sensor. To prevent excess negative pressure from forming, in some embodiments a second, passive valve is included providing a path for air to enter the chamber when the pressure of the chamber is below the atmospheric chamber, for example as the chamber cools air would enter the chamber through a one-way valve thereby preventing the water in the case of a bubbler, from being sucked into the chamber. Alternately a solenoid valve may be placed in the open position when the chamber pressure is detected as negative or the chamber is being cooled.

In some embodiments the mass flow is derived using a volumetric flow that quantizes gas volume with an unknown scale factor supplemented with a measurement of mass. For example, an un-calibrated airlock-bubbler commonly used for at-home beer brewing is used to measure volume of gas released from the chamber. To make use of such an un-calibrated flow measurement the mass of the charge is measured before placement in the chamber and again after the decarboxylation process has completed. The weight post-decarboxylation will be less by the amount of any water vapor driven off as the cannabis was heated to above the boiling point of water, and the reduction in mass due to the carbon dioxide released in the conversion of the cannabinoid-acid to the corresponding neutral form. While the two gasses have different molecular weights the water vapor is driven off around 100 degrees C., as the vapor pressure of water is 1 atmosphere at this condition and the CO2 is driven off substantially faster at higher temperatures. Thus, given two known gasses (water vapor and carbon dioxide) which are released at different rates at different temperatures, the total mass lost as measured directly by a scale may be apportioned between moisture and carbon dioxide by the integral of the flow meter output in conjunction with a known temperature of the charge during the time that the volumetric flow measurements were taken using a system of linear or linearized equations. In some embodiments the charge is first thoroughly dried, for example in a desiccation chamber using calcium chloride as a desiccant. By removing moisture from the charge all gasses released during the decarboxylation cycle will be carbon dioxide, the molecular weight of which is known. In some embodiments the gasses from the port are cooled to a known temperature before entering the volumetric flow meter, or the temperature is measured, so that the volumetric flow rate may account for the variable density of gas over temperature thereby maintaining accuracy in mass-flow estimation.

Figure 4:
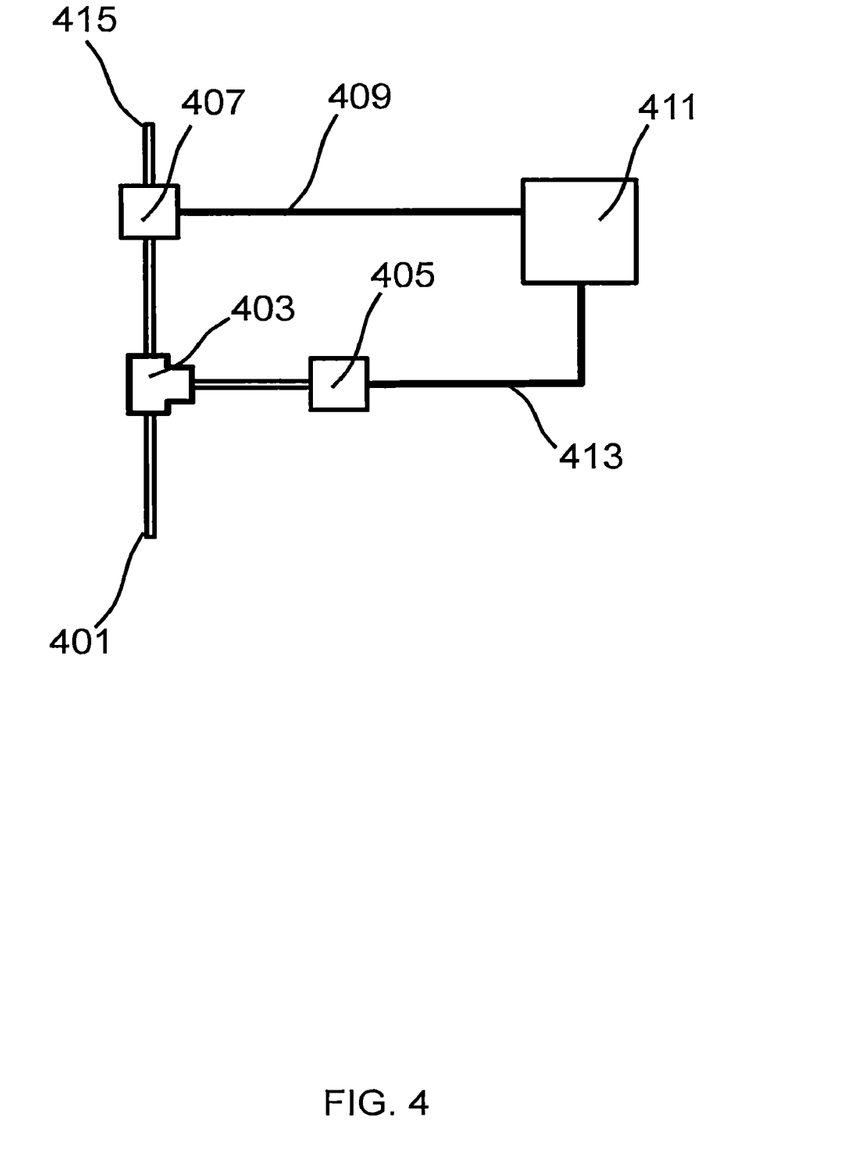
FIG. 4 illustrates a schematic diagram of an exemplary mass-flow detection system.

FIG. 4 illustrates a schematic diagram of an embodiment of a mass-flow detection system. Input 401 is coupled to the interior of the decarboxylation chamber (e.g. via port 115 or 309) so that gasses generated during the decarboxylation process may flow into the mass-flow detection system. Input 401 is further coupled to T-junction 403 coupled in turn to both pressure sensor 405 and valve 407. Valve 407 may be a normally-open or normally-closed valve and is controlled using an electrical signal 409 generated using processor 411 and, optionally, a relay or transistor. When open, valve 407 allows gasses at the input of valve 407 (e.g. at T-junction 403) to couple to the atmosphere via vent 415. Processor 411 monitors the output 413 of pressure sensor 405; upon reaching a pressure threshold, processor 411 activates the valve via electrical signal 409 thereby dropping the pressure. A variable on the processor is used to maintain track of the number of times the valve was opened, the pressure drop when the valve opened and then reclosed, or a combination thereof. Alternately, processor 411 maintains valve 407 in the open position and periodically closes the value while monitoring the pressure when the valve is closed. Gas generation rate is determined in this case by the increase in pressure versus time; after a period of measurement the valve is returned to the open state. A variable on the processor is used to maintain track of the number of times the valve was opened, or the pressure drop when the valve closed and then reopened; these measurements are combined to account for the total amount of gas released between instants of measurement, using for example interpolation, extrapolation, integration, or totalization.

Figure 5:
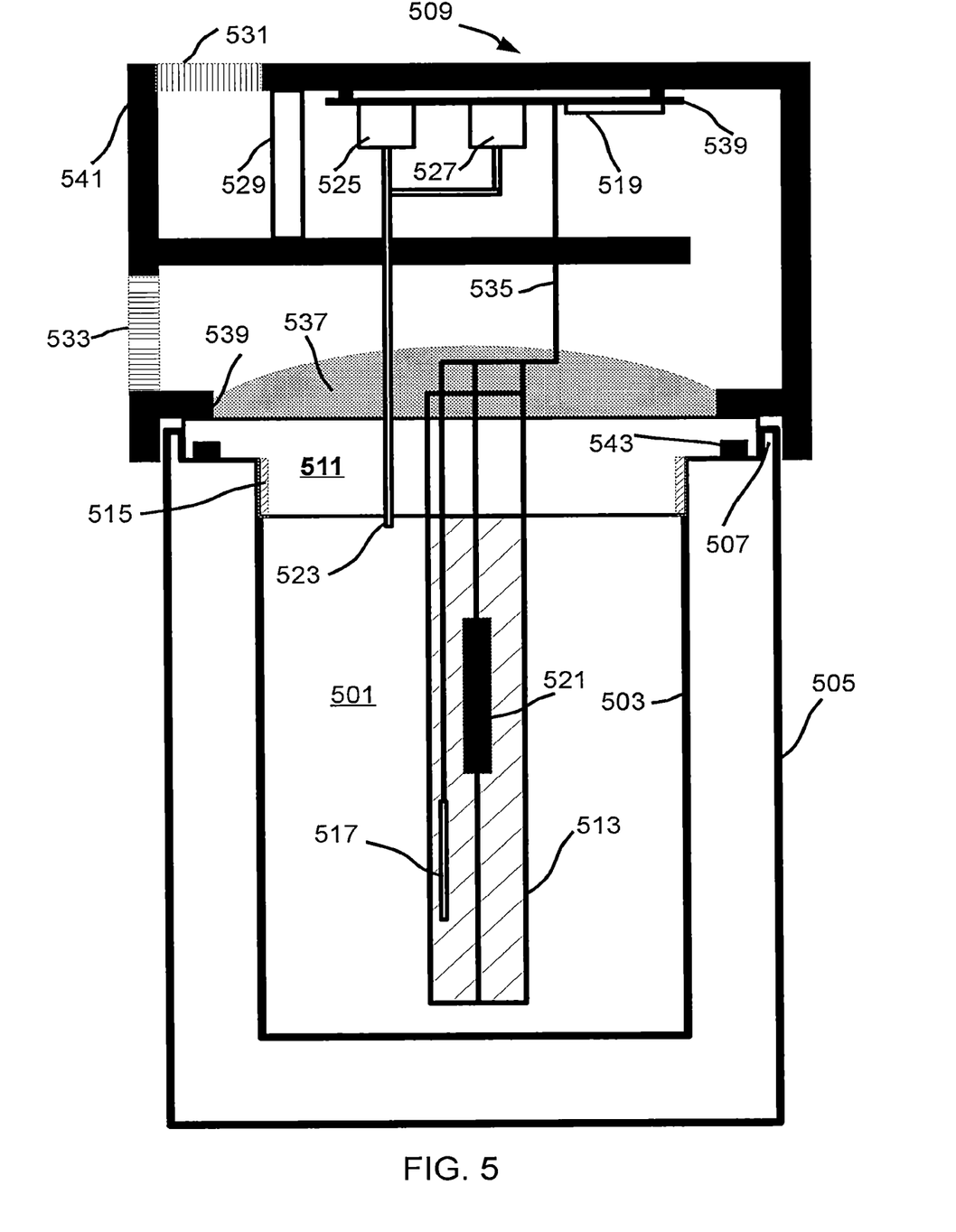
FIG. 5 illustrates a fourth embodiment of a decarboxylator.

FIG. 5 shows a decarboxylation chamber with a lid having processing and control circuitry. Chamber 501 has an inner wall 503 and an outer wall 505 separated from each other with a vacuum space; the inner and outer walls are formed of metal (e.g. stainless steel) and are attached at the rim 507; in some embodiments the inner and outer walls are attached to a material having lower thermal conductivity than the materials 503 and 505 (e.g. A phenol-formaldehyde resin) as opposed to directly in contact. Lid 509, comprising a thermally-insulating material such as a plastic, is coupled at coupling point 539 (using e.g. a screw, a rivet, a clasp, a barb, an adhesive, etc.) to thermally conductive plate 511 and an optional thermally conductive tube 513 that protrudes into the decarboxylation chamber thereby improving heat transfer characteristics. The conductive plate 511 makes physical contact with threads 515 in the inner wall 503 thereby forming a thermal bridge allowing heat to be transferred from the conductive plate to the inner chamber walls. The temperature of plate 511 is measured with temperature sensor 517 (e.g. a thermocouple, thermistor, diode) the output of which is coupled to processor 519. In some embodiments the temperature sensor is located in tube 513, on plate 511, or multiple temperature sensors are used to monitor or control the temperature uniformity throughout the chamber. Heat is applied to the conductive plate 511 or tube 513 using a dissipative element such as a resistor or a nonlinear resistor 521 thermally coupled to either plate 511 or tube 513 using a mechanical interface (e.g. clamp, physical contact), a thermal grease, or a combination thereof. Processor 519 is coupled to a circuit board 539, and receives an input from the temperature sensor through cable 535 (comprising a plurality of conductors) and controls energy to the heating element 521 using an output such as a general-purpose-input-output pin (GPIO pin) coupled to a transistor or a relay, as processor outputs generally have insufficient drive capability to energize a heater of more than a fraction of a Watt directly. The processor further monitors the pressure inside the chamber 501 via a port 523 (e.g. metal tube, silicone tube) that couples the inner chamber to pressure sensor 525. Processor 519 also is coupled to valve 527 that, when opened, provides a path for gasses under greater than ambient pressure to escape from inside the chamber. During the decarboxylation process the pressure is monitored and the valve is controlled in concert with the output of the pressure sensor to monitor or quantify the rate of gas generation within the chamber by the charge in a manner similar to that described earlier. Because tube 513 or plate 511 may get hot during operation the operator is shielded from direct contact by an insulating guard 541 made of a material having lower conductivity than the tube or plate, such as a thermoset plastic. Guard 541 also provides a mechanical structure for supporting (e.g. by screws, snaps) various components such as a pressure sensor, a valve, a processor, etc. in the lid at a temperature lower than the temperature of the tube or plate thereby improving reliability and performance of the components. In some embodiments a fan 529 (e.g. a fan similar to a fan used for cooling a microprocessor) is energized as appropriate by the processor to maintain a component (e.g. processor, sensor, actuator) below a maximum temperature. In some embodiments the fan is energized to increase the rate of cooling of plate 511 or tube 513, or to apply a thermal (e.g. heat) bias similar to a class-A amplifier in electronics. Insulation 537 above plate 511 provides an additional degree of freedom to control the heat loss from the chamber, in conjunction with fan control, as well as reduce the amount of heat transferred to the electrical components. Input grille 531 and output grille 533 provide input and output vents so cool air may be circulated by the fan 529 past the electronics, and then past the top or tube. Seal 543 makes contact between the lid and the chamber rim thereby forcing any gas exchange to occur through the port 523.

Figure 6:
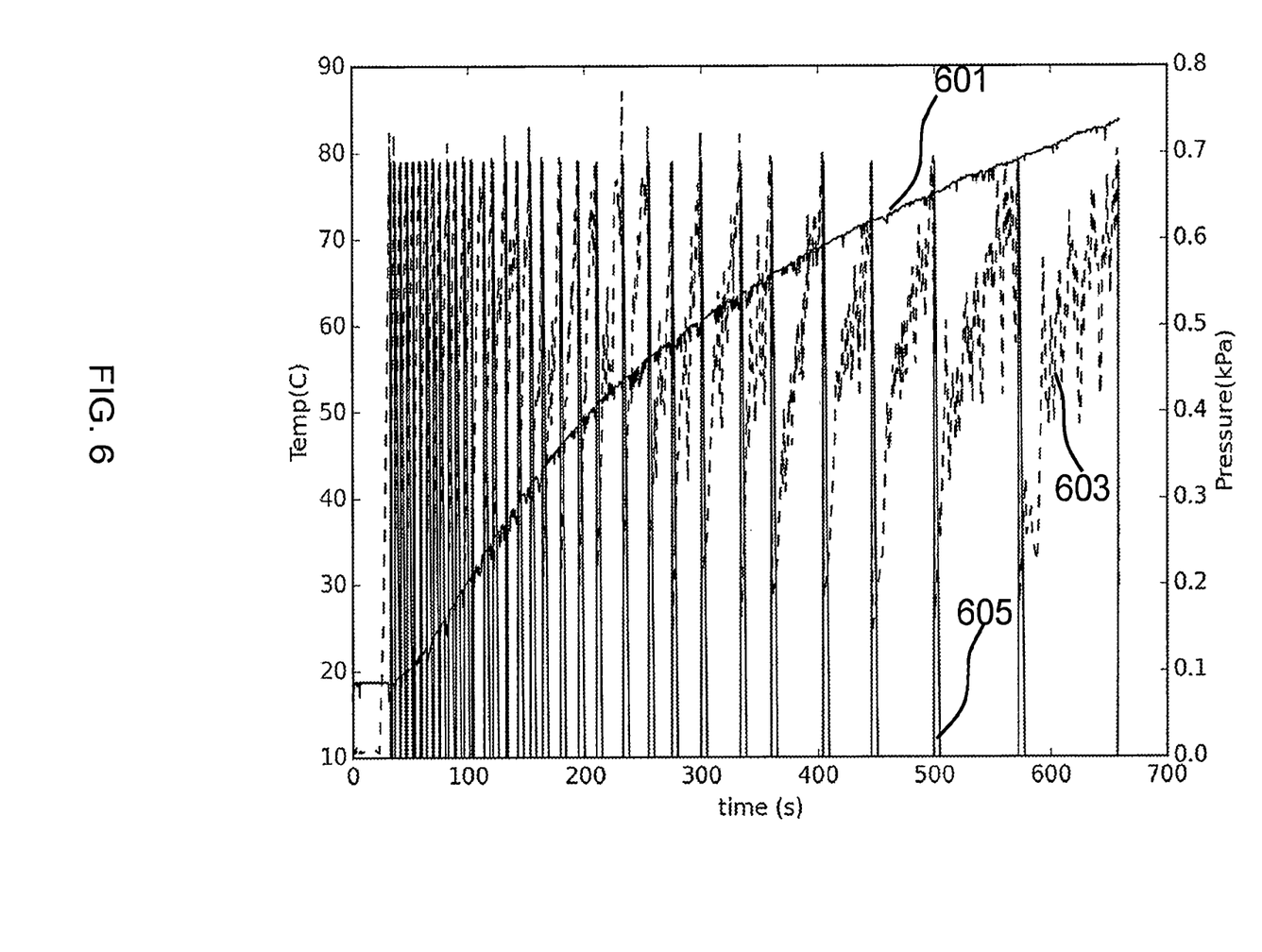
FIG. 6 illustrates various state variables as an empty chamber was heated.

FIG. 6 shows measured temperature in Celsius (601), pressure in kPa (603), and valve position (605) where 0 indicates a closed valve position with the valve otherwise open, as an empty, one-pint volume was heated from room temperature to an elevated temperature. A processor was configured to monitor the pressure and open the valve for 0.5 seconds when the pressure reached 0.7 kPa gauge pressure, thereby releasing the pressure. As can be seen from FIG. 6 the valve was opened about 33 times as the temperature rose from ambient to about 83 degrees C. In this example the valve was only opened for 0.5 seconds, so the pressure doesn't drop fully to ambient; therefore, the amount of mass removed during the release portion of the cycle may be more accurately estimated using the pressure before the valve is opened, the pressure after the valve is closed, and the chamber temperature to determine the amount of gas (e.g. mass, or mole fraction) released during the time the valve is open using the ideal gas law. Furthermore, as the temperature rises, the mass of gas released per release cycle (e.g. every time the pressure reaches 0.7 kPa the valve is opened to release gas), will drop because the density of a hot gas is lower than a cool gas. Accurate mass estimation takes the varying density of the released gas over temperature to provide a more accurate estimate of mass of the released gasses, accounting for the fact that the density of gas released over temperature is variable function of temperature.

Figure 7:
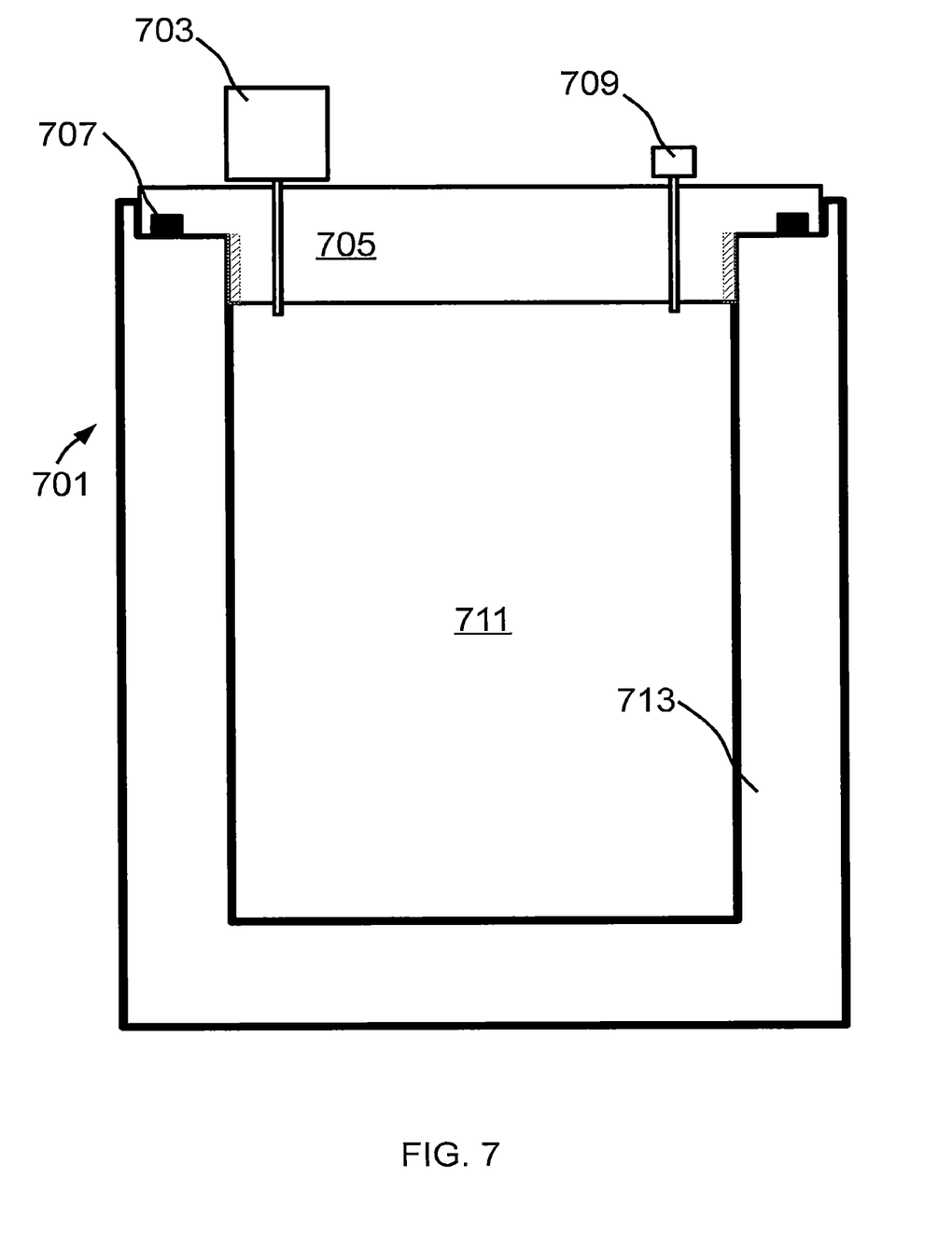
FIG. 7 illustrates a fifth embodiment of a decarboxylator comprising a sealed chamber.

With reference to FIG. 7, in some embodiments the gas generation is inferred using a closed pressure vessel 701, having a pressure sensor 703, as the decarboxylation chamber. The charge is placed in the chamber 711, the lid 705 is sealed with a seal 707, the chamber heated to a decarboxylation temperature above 100 degrees C., and the pressure monitored. An optional safety valve 709 opens when pressure exceeds the design capacity of the chamber providing protection in the event of an overpressure condition. The chamber walls 713 may be of a double-walled construction with an insulated interior, such as a vacuum flask, with heat applied via a heated portion of the lid or a thermally-conductive tube protruding into the chamber; alternately, the chamber walls 713 may be of a solid construction, e.g. aluminum, suitable for conducting externally provided heat such as a household or commercial oven. After thermal equilibrium has been reached in the chamber there will be a component of the pressure that is due to moisture in the charge; this component is a function of the vapor pressure of water at temperature and does not increase during the decarboxylation process. However, as decarboxylation generates carbon dioxide the chamber pressure will rise. After the decarboxylation process has ceased, as determined by the change of pressure over time dropping below a threshold, the container is cooled back to the same temperature at which it started. The pressure is noted and, in conjunction with the known volume of the chamber, indicates the amount of carbon dioxide gas generated during the decarboxylation process according to (deltaPV/RT)=n where n is the number of moles of CO2 gas created. Since each molecule of CO2 released corresponds to a molecule of cannabinoid acid being converted to the neutral form the total number of molecules, and hence mass, of converted acid-cannabinoid may be estimated given the molecular weight of the target cannabinoid. In some embodiments the initial and final temperatures are different and are compensated for using measured values of the initial and final temperatures in conjunction with the ideal gas law. After measurement, the pressure is released using a release valve coupled to the chamber (e.g. via the pressure sensor, the safety valve, or an additional valve for this purpose) and the container opened.

Thus the acid-cannabinoid has been fully decarboxylated and the amount of acid-cannabinoids converted to the neutral form quantified.

Figure 8:
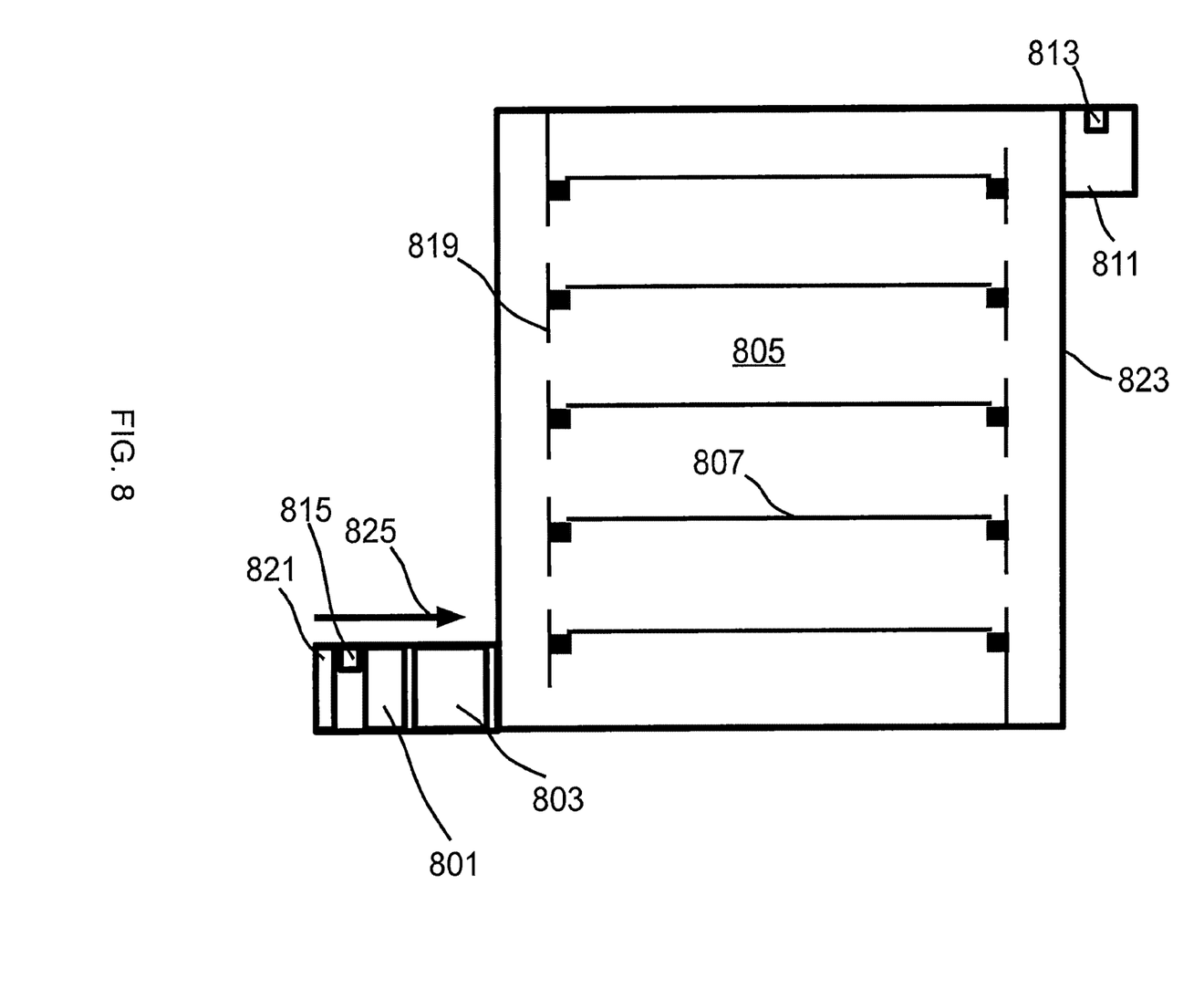
FIG. 8 illustrates a sixth embodiment of a decarboxylator comprising a forced-air heater.

With reference to the schematic diagram of FIG. 8, in some embodiments a fan 801 blows air in a direction 825 past a heating element 803 into a decarboxylation chamber 805; the air is filtered in some embodiments by a HEPA filter 821. In some embodiments a non-oxidizing gas such as dry nitrogen or argon is used in place of air as an input to heating element 803. In some embodiments the air is heated in a manner similar to a household hair-dryer, with an electrical filament; however, larger commercial or industrial-scale decarboxylation operations may use any suitable manner for providing heat, such as natural gas, an electrical furnace, heat pump, waste steam, etc. Plant material to be decarboxylated is placed on trays 807 having a mesh bottom thereby allowing the heated air to penetrate the plant material. Baffles 819 help evenly distribute the air across the chamber thereby ensuring more even decarboxylation. The output of the chamber is vented through an exhaust port 811. In some embodiments the chamber walls 823 are insulated using foam, fiberglass batting, vacuum like a Dewar flask, or any other appropriate insulation. The hot air, typically having a temperature greater than 100 degrees C., is blown by or through the plant matter causing decarboxylation to occur, thereby releasing carbon dioxide in the process. A first carbon dioxide detector 813 measures the carbon dioxide concentration at the port and determines decarboxylation is complete when the carbon dioxide level drops below a threshold, e.g. 500 ppm. In some embodiments a second carbon dioxide sensor 815 is placed in the air flow before the decarboxylation chamber so that the amount of CO2 generated by decarboxylation may be determined irrespective of the ambient CO2 levels which may vary, especially in enclosed spaces. In some embodiments the CO2 sensor has a full-scale value of 0.1% to a few percent CO2 and uses infrared radiation to detect CO2 for example a nondispersive infrared sensor. The first and second CO2 sensors are zero-calibrated by measuring the CO2 sensor outputs with an empty chamber; since no CO2 is being generated between the first and second sensors and the difference between the two sensors may be used to zero or tare the measurement of CO2 generation in the chamber. In some embodiments the air at the output of the chamber is sampled with a tube, the tube cooling the exhaust to near the input temperature to avoid temperature sensitivity of the CO2 sensor from adding errors to the measurement. Measurement of the carbon dioxide level at the port, in conjunction with the mass flow rate of the exhaust gas at the output allows the amount of carbon dioxide generated during the decarboxylation process to be integrated allowing the amount of acid-cannabinoid converted to the neutral form to be calculated. In conjunction with the initial or final mass of the plant material, a percentage of neutral-form cannabinoid may thus be calculated. Mass flow rate at the exhaust port may be accomplished using a differential pressure sensor and a Venturi tube, a turbine flow meter, an assumed density of air, a measurement of the temperature at the exhaust port, or any other appropriate method for measuring flow.

In some embodiments a fat such as clarified butter, coconut oil, cacao butter, etc. is placed in the chamber with the charge. Inclusion of a fat or oil with the charge allows cannabinoids to be dissolved in the fat or oil during decarboxylation after which the fat or oil is drained from the plant matter and is ready for use.

The embodiments, techniques, components, connections, and other teachings described herein are examples and were chosen to provide a clear explanation without unnecessary obfuscation. The scope of coverage is not intended to be limited to the specific exemplary teachings set forth herein, but rather the scope of coverage is set forth by the claims listed below.

The invention claimed is:

1. A method for processing plant material comprising:
providing a quantity of material, the material including a cannabinoid acid;
decarboxylating at least a portion of the cannabinoid acid by applying an elevated temperature to the material thereby increasing a rate of decarboxylation;
detecting, with a sensor having an output, carbon dioxide released during decarboxylation; and,
processing the sensor output to estimate a quantity of a cannabinoid or a quantity of a cannabinoid acid in the provided material.

2. The method of claim 1 wherein the step of applying an elevated temperature comprises forcing a heated gas past the provided material.

3. The method of claim 1 wherein the step of detecting carbon dioxide with a sensor comprises measuring carbon dioxide concentration.

4. The method of claim 1 wherein the step of detecting carbon dioxide with a sensor comprises measuring a pressure.

5. The method of claim 1 wherein the step of applying an elevated temperature further includes regulating the temperature to a desired value.

6. The method of claim 1 wherein the step of estimating a quantity of a cannabinoid or a quantity of a cannabinoid acid comprises estimating one of: decarboxylation completeness; or, a rate of decarboxylation.

7. The method of claim 1 further including:
a step of sealing a chamber with a lid before the step of applying an elevated temperature.

8. The method of claim 7 wherein:
the chamber remains sealed until the temperature returns to ambient conditions; and,
wherein the step of detecting carbon dioxide with a sensor comprises measuring a pressure.

9. The method of claim 1 wherein the cannabinoid acid is selected from one of THCA, CBDA, CBGA, and the cannabinoid is a neutral-cannabinoid selected from one of THC, CBD, or CBG.

10. The method of claim 1 wherein the processing is performed by a processor.

11. A system for processing plant material comprising:
a chamber having an opening;
a heater operative to heat contents of the chamber;
a pressure sensor having an output, the sensor being coupled to the chamber; and,
a processor coupled to the pressure sensor output and configured to process the pressure sensor output to provide information about a quantity of a cannabinoid or a quantity of a cannabinoid acid.

12. The system of claim 11 wherein the quantity of a cannabinoid or a quantity of a cannabinoid acid comprises a quantity of a first neutral- or acid-cannabinoid and a quantity of a second neutral- or acid-cannabinoid.

13. The system of claim 11 wherein the quantity of a cannabinoid or a quantity of a cannabinoid acid comprises at least one selected from the following list: information about remaining cannabinoid acids in the chamber; information about cannabinoid acids in the chamber; information about neutral cannabinoids in the chamber; a rate of decarboxylation; or, an indication of the completeness of decarboxylation.

14. The system of claim 11 wherein the cannabinoid acid is selected from one of THCA, CBDA, CBGA, and the cannabinoid is a neutral-cannabinoid selected from one of THC, CBD, or CBG.

15. The system of claim 11 wherein the plant material is selected from the group consisting of: *Acmella oleracea, Cannabis sativa, Cannabis sativa* forma indica, *Echinacea, Helichrysum umbraculigerum*, and *Radula marginata*.

16. The system of claim 11 further including a valve.

17. The system of claim 11, further including:
a lid;
a seal;
wherein the pressure sensor is coupled to an interior of the chamber via a port; and,
wherein the processor is further configured to measure an increase in pressure in response to decarboxylation of cannabinoid acids using the sensor.

18. The system of claim 17, wherein the processor is further configured to use the increase in pressure in conjunction with a volume of the chamber as part of the processing of the pressure sensor output to provide information about a quantity of a cannabinoid or a quantity of a cannabinoid acid.

19. The system of claim 11 further including a temperature sensor;
wherein the processor is further configured to:
control a chamber temperature to vary between at least two temperatures while monitoring the temperature with the temperature sensor; and,
process the sensor output responsive to carbon dioxide to detect a property of at least two different cannabinoids in the chamber.

20. The system of claim 11 further including:
a second sensor responsive to temperature coupled to the chamber and the processor;
wherein the processor controls the heater using at least the second sensor.

21. The system of claim 11, further including a lid with a seal.

22. The system of claim 21, wherein the processor is further configured to count bubbles; and,
wherein the information about a quantity of a cannabinoid or a quantity of a cannabinoid acid is determined by the processor using the count of bubbles.

23. The system of claim 21, wherein the processor is further configured to:
measure an increase in pressure due to decarboxylation of cannabinoid acids, using the sensor; and,
wherein the information about a quantity of a cannabinoid or a quantity of a cannabinoid acid is determined by the processor using the increase in pressure in conjunction with a volume of the chamber.

* * * * *